United States Patent [19]
Muralidhara et al.

[11] Patent Number: 5,847,238
[45] Date of Patent: Dec. 8, 1998

[54] PROCESSES FOR RECOVERING XANTHOPHYLLS FROM CORN GLUTEN MEAL

[75] Inventors: Harapanahalli S. Muralidhara, Plymouth; Tracy Lee Cornuelle, St. Paul, both of Minn.

[73] Assignee: Cargill, Incorporated, Minneapolis, Minn.

[21] Appl. No.: 770,374

[22] Filed: Nov. 29, 1996

Related U.S. Application Data

[63] Continuation-in-part of Ser. No. 486,376, Jun. 7, 1995, Pat. No. 5,602,286.

[51] Int. Cl.$^6$ ................................................ C07C 568/816
[52] U.S. Cl. .............................................................. 568/816
[58] Field of Search ............................................... 568/816

[56] References Cited

U.S. PATENT DOCUMENTS

| | | | |
|---|---|---|---|
| 3,081,171 | 3/1963 | Reiner | 99/2 |
| 3,997,679 | 12/1976 | Salkin | 426/250 |
| 4,077,950 | 3/1978 | White | 260/112 |
| 4,153,734 | 5/1979 | Huchette | 426/250 |
| 4,233,210 | 11/1980 | Koch | 260/112 R |
| 4,267,038 | 5/1981 | Thompson | 210/602 |
| 4,304,792 | 12/1981 | Sreenivasam et al. | 426/250 |
| 4,320,050 | 3/1982 | Rebeller et al. | 260/112 R |
| 4,351,346 | 9/1982 | Brummer et al. | 131/276 |
| 4,680,314 | 7/1987 | Nonomura | 514/725 |
| 4,851,339 | 7/1989 | Hills | 435/67 |
| 5,139,809 | 8/1992 | Wienen et al. | 426/578 |
| 5,254,673 | 10/1993 | Cook et al. | 530/373 |
| 5,308,759 | 5/1994 | Gierhart | 435/67 |
| 5,320,669 | 6/1994 | Lim et al. | 106/157 |
| 5,382,714 | 1/1995 | Khachik | 568/834 |
| 5,427,783 | 6/1995 | Gierhart | 424/93.4 |
| 5,510,463 | 4/1996 | Takahashi et al. | 530/373 |
| 5,580,959 | 12/1996 | Cook et al. | 530/373 |

Primary Examiner—Samuel Barts
Attorney, Agent, or Firm—Fitch, Even, Tabin & Flannery

[57] ABSTRACT

Improved methods for the recovery of xanthophylls from corn gluten meal are provided. More specifically, methods for the recovery of xanthophylls from corn gluten whereby relatively dry corn gluten is extracted with an organic alcohol followed by a saponification reaction to convert xanthophyll esters to xanthophylls is described. Also described are methods for the recovery of xanthophylls from corn gluten meal whereby relatively dry corn gluten meal is extracted with a first solvent containing and antioxidant and the resulting extract is, optionally, purified. Using these is methods, xanthophylls can be recovered from corn gluten meal in higher yields, at greater efficiencies, and in higher purity as to compared to prior art methods. Moreover, the xanthophyll products recovered in these methods are ideally suited for use in food products and in pharmaceuticals. These materials are especially suited for use in poultry feeds to provide the desired, healthy yellow color or hue in broiler and egg yolks.

31 Claims, 5 Drawing Sheets

PROCESSES FOR RECOVERING XANTHOPHYLLS FROM CORN GLUTEN MEAL

FIELD OF THE INVENTION

This Application is a Continuation-in-Part Application of application U.S. Ser. No. 08/486,376, filed on Jun. 7, 1995 now U.S. Pat. No. 5,602,286.

This invention provides improved methods for the recovery of xanthophylls from corn gluten meal. Using the methods of this invention, the yield, recovery efficiency, and quality of the recovered xanthophylls are significantly improved.

BACKGROUND OF THE INVENTION

Xanthophylls are oxygenated carotenoid compounds occurring in green vegetation (e.g., corn, marigolds, and the like) and in some animal products (most notably egg yolks). The xanthophylls are yellow pigments which can be used in both animal and human foods and in pharmaceuticals. The xanthophylls in natural feed sources are used often to provide natural pigmentation for poultry (especially chickens) and their eggs. Examples of such natural feed sources include yellow corn, corn gluten meal, marigold meal, and algal meal. Such xanthophyll-containing materials impart the desirable healthy yellow color or hue to broiler chickens when included in chicken feed.

Use of natural feed sources to provide xanthophylls can lead to inconsistent results, mainly observable in the variation of color levels obtained in broiler chickens. In many cases, such natural feed sources can differ greatly in the bioavailability of the xanthophylls, the xanthophyll content, and xanthophyll stability. These problems often result in poor correlation between the chemical analysis of the feed material (i.e., amount of xanthophylls present) and the biological performance (i.e., color development in the broiler).

Attempts have been made to extract xanthophylls from vegetable matter such as corn and marigold meals. For example, Soviet Patent Application 1,819,619 provides a method for the extraction of flavonoids and carotenoids from marigold petals. The petals are ground and then extracted seven times with ethanol at 70° C. for 40 minutes per extraction. After distilling off the alcohol, the extract is dissolved in castor oil. This material generally contains about 30 weight percent flavonoids (e.g., patuletin, patuletrin, quercetagetin, quercetagetrin, and quercetin) and about 15 weight percent carotenoids (e.g., xanthophyll, rubsanthin, helenien, carotene, and violazanthine) from the original marigold petals. This material was used for medicinal purposes. Most commercial xanthophylls in use today are derived from marigold petals and are, as a result, relatively expensive.

More recently, Cook et al., U.S. Pat. No. 5,254,673 (Oct. 19, 1993), provided a method for treating corn gluten meal to purify corn zein. Pigments, including xanthophylls, were generated as by-products. Wet or gently dried corn gluten was subjected to a combination of enzymatic starch hydrolysis, alkaline treatment and alcohol washing, followed by either alcohol extraction or fractionation of the deflavored and decolored gluten. Pigments were reported to be recovered in the alcohol washing step which consisted of washing in "a continuous counter-current fashion or by batch-wise washing with fresh alcohol at each step." No details were given in regard to the amounts or quality of the recovered by-product pigments.

We have now duplicated the Cook et al. method using corn gluten meal (containing about 12 weight percent moisture). Xanthophylls recovered by the method described by Cook et al. generally have a rubber-like or paste-like consistency. In contrast, the xanthophylls recovered by methods within the present invention are a crystalline, powdered material with a stronger yellow color. Moreover, xanthophylls are recovered by the Cook et al. method in significantly lower yields and at significantly lower efficiencies as compared to the recovery methods of the present invention. Xanthophylls recovered by the Cook et al. method must undergo significant further purification (with decreasing yields) to obtain xanthophylls which can be used in food products. Xanthophylls produced by methods within this invention are suitable for use in food products with significantly less further purification.

It would be desirable to recover xanthophylls from a natural source such as corn gluten meal in high yields and efficiencies. It would desirable to obtain xanthophylls as a crystalline powder from a natural source such as corn gluten meal. It would also be desirable to obtain xanthophylls from a natural source such as corn gluten meal in a purity suitable for use in food products. The methods of the present invention provide such xanthophylls.

SUMMARY OF THE INVENTION

The present invention relates to improved methods for the recovery of xanthophylls from corn gluten meal.

In one aspect ("Process I"), the present invention relates to a method for the recovery of xanthophylls from corn gluten meal whereby relatively dry corn gluten meal is extracted with an organic alcohol followed by a saponification reaction to convert xanthophyll esters to xanthophylls. Using this method of the invention, xanthophylls can be recovered from corn gluten meal in higher yields, in greater efficiencies, and in higher purity as compared to prior art methods. Moreover, the xanthophylls recovered in this method of the invention are a crystalline, powdery solid ideally suited for use in food products and pharmaceuticals.

In a second aspect ("Process II"), the present invention relates to a method for the recovery of xanthophylls from corn gluten meal whereby corn gluten meal containing less than about 30 weight percent moisture is extracted with an organic solvent (or a mixture of organic solvents) to which an antioxidant has been added, and the resulting crude xanthophylls which are present in the soluble portion of the extract are collected and may be purified in order to increase the purity of the final xanthophylls product. Unlike the Process I method of the invention, this method of the invention does not employ a saponification reaction. Also, in contrast to the Process I method of the invention, this method of the invention employs an antioxidant in the solvent (or solvent mixture) which is used to extract xanthophylls from the corn gluten meal to produce crude xanthophylls, and preferably employs higher temperatures than the Process I method of the invention. Using this method of the invention, xanthophylls can also be recovered from corn gluten meal in higher yields, in greater efficiencies and in higher purity as compared to other methods for recovering xanthophylls from corn gluten meal. The xanthophylls recovered in this method of the invention are in the form of an orange or red paste which may be used in food products and in pharmaceuticals. This method of the invention is more preferable than the Process I method because the yields of purified xanthophylls are generally higher.

One object of the present invention is to provide a method for recovering xanthophylls from corn gluten meal, said method comprising:

(1) drying corn gluten meal to a water content of less than about 12 weight percent;

(2) extracting the dried corn gluten meal with a first alcohol;

(3) collecting the extract containing crude xanthophylls from step (2) to obtain the crude xanthophylls;

(4) treating the crude xanthophylls with a second alcohol containing a base;

(5) removing the second alcohol from the treated crude xanthophylls to recover refined xanthophylls; and (6) collecting the refined xanthophylls (Process I).

Preferably, the refined xanthophylls are further purified by techniques such as adsorption chromatography or ion exchange chromatography.

Another object of the present invention is to provide a method for recovering xanthophylls from corn gluten meal, said method comprising:

(1) extracting corn gluten meal containing less than about 12 weight percent moisture with a first alcohol;

(2) collecting the extract containing crude xanthophylls from step (1) to obtain the crude xanthophylls;

(3) treating the crude xanthophylls with a second alcohol containing a base;

(4) removing the second alcohol from the treated crude xanthophylls to recover refined xanthophylls; and (5) collecting the refined xanthophylls (Process I).

Preferably, the refined xanthophylls are further purified by techniques such as adsorption chromatography or ion exchange chromatography.

A further object of the present invention is to provide a method for recovering xanthophylls from corn is gluten meal, said method comprising:

(1) extracting corn gluten meal containing less than about 12 weight percent moisture with a first alcohol;

(2) collecting the extract containing crude xanthophylls from step (1) to obtain the crude xanthophylls;

(3) treating the crude xanthophylls with a second alcohol containing a base to convert any xanthophyll esters into xanthophylls;

(4) removing the second alcohol from the treated crude xanthophylls to recover refined xanthophylls;

(5) purifying the refined xanthophylls by chromatography or ion exchange techniques; and (6) collecting the purified refined xanthophylls (Process I).

Another object of the present invention is to provide a method for recovering xanthophylls from corn gluten meal, said method comprising:

(1) extracting corn gluten meal containing less than about 30 weight percent moisture with an organic solvent, or an organic solvent mixture, containing an amount of antioxidant which is less than about 0.5 weight percent of the total amount of xanthophylls present in the corn gluten meal in a ratio of at least about 2:1 of organic solvent, or organic solvent mixture, to corn gluten meal; and (2) collecting the resulting extract to obtain the xanthophylls (Process II).

Preferably, the xanthophylls obtained are purified by techniques such as normal phase adsorption chromatography.

Yet another object of the present invention is to provide a method for recovering xanthophylls from corn gluten meal, said method comprising:

(1) extracting corn gluten meal containing less than about 30 weight percent moisture with an organic solvent, or an organic solvent mixture, containing an amount of antioxidant which is less than about 0.5 weight percent of the total amount of xanthophylls present in the corn gluten meal in a ratio of at least about 2:1 of organic solvent, or organic solvent mixture, to corn gluten meal;

(2) collecting the resulting extract to obtain crude xanthophylls;

(3) purifying the crude xanthophylls; and (4) collecting the purified xanthophylls (Process II).

Still another object of the present invention is to provide a method for recovering xanthophylls from corn gluten meal, said method comprising:

(1) drying a sample of corn gluten meal to a moisture content of less than about 30 weight percent;

(2) adding an amount of antioxidant to an organic solvent, or to an organic solvent mixture, which is less than about 0.5 weight percent of the total amount of xanthophylls present in the sample of corn gluten meal;

(3) extracting the sample of corn gluten meal with the organic solvent, or organic solvent mixture, by mixing a ratio of organic solvent, or organic solvent mixture, to corn gluten meal of at least about 2:1 for a period of time ranging from about 10 minutes to about 90 minutes at a temperature ranging from about 10° C. to about 80° C.;

(4) collecting the resulting extract to obtain crude xanthophylls;

(5) purifying the crude xanthophylls; and (6) collecting the purified xanthophylls (Process II).

These and other objects and advantages of the present invention will become apparent through the following description of the drawings and preferred embodiments of the invention.

DESCRIPTION OF THE PREFERRED EMBODIMENTS

The present invention provides improved methods for recovering xanthophylls from corn gluten meal.

The Process I method of the present invention provides a method for the recovery of xanthophylls from corn gluten meal whereby relatively dry corn gluten meal is extracted with an organic alcohol followed by a saponification reaction to convert xanthophyll esters to xanthophylls. The Process II method of the present invention provides a method for the recovery of xanthophylls from corn gluten meal whereby relatively dry corn gluten meal is extracted with an organic solvent containing an antioxidant, and the resulting crude xanthophylls product is, optionally, purified to produce a purified xanthophylls product. When normal phase adsorption chromatography is employed as the purification method in the optional purification step, the "crude xanthophylls" product obtained when the extract is collected should be converted into a "refined xanthophylls" product by removing protein from the "crude xanthophylls." Then, the resulting "refined xanthophylls" product may be purified to produce a purified xanthophylls product.

Using the Process I and Process II methods of this invention, xanthophylls can be recovered from corn gluten meal in higher yields, in greater efficiencies, and in higher purity as compared to prior art methods. Moreover, the xanthophylls recovered in the Process I method of this invention are in the form of crystalline, powdery solids, and the xanthophylls recovered in the Process II method of the invention are in the form of an orange or red paste, each of which is ideally suited for use in food products and pharmaceuticals.

The xanthophylls-containing source for the practice of the Process I and Process II methods of the present invention is corn gluten meal. Corn gluten meal is the primary by-product of commercial corn wet milling. The corn gluten meal used in the Process I and Process II methods of the invention should be relatively dry. By "relatively dry," it is meant for the Process I method of the invention, that the corn gluten meal contains less than about 12 weight percent water and, more preferably, contains less than about 10 weight percent water, and for the Process II method of the invention, that the corn gluten meal contains less than about 30 weight percent water and, preferably, contains less than about 20 weight percent water and, more preferably, contains less than about 12 weight percent water. If wet corn gluten meal (i.e., greater than about 12 weight percent moisture for the Process I method of the invention, or greater than about 30 weight percent moisture for the Process II method of the invention, or where significant water is added to the corn gluten meal) is used in the Process I and Process II methods of the present invention, significantly reduced extraction efficiencies of the xanthophylls will be obtained by these two methods. Moreover, the xanthophylls obtained will have a rubber-like consistency. The corn gluten meal can be dried to the desired moisture content by conventional means known by those of skill in the art. Generally, dried corn gluten meal contains from about 100 to 200 mg xanthophylls per pound of corn gluten meal.

All of the reagents and equipment employed in the Process I and Process II methods of the present invention are commercially available. Sources for these reagents and equipment include Aldrich Chemical Company (Milwaukee, Wis.), Fisher Scientific (Pittsburgh, Pa.), Glitsch (Houston, Tex.), Crown Iron Works Co. (Minneapolis, Minn.), Ace Glass, Inc. (Vineland, N.J.), Millipore Corporation (Bedford, Mass.) and PCI Membrane Systems (Whitchurch, Hampshire, England).

Process I Method

In the first major step of the Process I method of the present invention, the relatively dry corn gluten meal is extracted with an alcohol in which the xanthophylls are slightly soluble. Suitable alcohols include methanol, ethanol, isopropyl alcohol, and butyl alcohols. Preferably, ethanol (industrial or absolute) and/or methanol are used in the solvent extraction process. Preferably, the alcohol contains less than about 20 weight percent water and, more preferably, less than about 10 weight percent water; extraction efficiencies decrease as the water content of the ethanol solvent increases above about 20 weight percent (see FIG. 2). Generally, the ratio of corn gluten meal to the alcohol solvent for the extraction is about 1 to 2. Generally, the solvent must be present in an amount sufficient to form a slurry. Generally, the extraction is carried out at ambient temperatures (i.e., about 20° to 30° C.) using conventional solvent extraction techniques. Temperatures above about 40° C. should be avoided as the extraction efficiency decreases dramatically (see FIG. 3). Especially preferred extraction techniques includes continuous extraction, counter-current extraction, co-current extraction, centrifugal extraction, and the like. The xanthophylls-containing extract (or combined extracts) is first filtered to remove insoluble materials and, preferably, then stripped of the solvent. Conventional stripping techniques such as distillation, vacuum distillation, sparging, rotary evaporation, and the like can be used. Solvent removal, if used, is not required to be complete since solvent is also used in the saponification step. Indeed, it is not necessary (although it is preferred) that the solvent be removed prior to the saponification step. The xanthophyll extract at this stage of the process generally contains about 800 to 1200 mg xanthophylls per pound of extract. This represents a concentration factor of about 7 to 8 as compared to the original corn gluten meal.

In the second major step of the Process I method of this invention, the xanthophyll extract is reacted with alcoholic base in a saponification reaction to convert the xanthophyll esters to free xanthophylls, thereby increasing the yield and efficiencies of xanthophyll recovery. This conversion is a conventional saponification reaction. Although alcoholic bases in general can be used, ethanolic bases are generally preferred. Generally, it is preferred that the same alcohol as used in the first extraction step is used throughout the process. Suitable bases include alkaline hydroxides such as lithium hydroxide, sodium hydroxide, and potassium hydroxide. Ethanolic potassium hydroxide is the most preferred saponification reactant. Saponification is preferably carried out by simply refluxing the xanthophyll extract in the alcoholic base for about 1 to 2 hours. After washing with additional alcohol (preferably ethanol), filtering, and stripping, refined xanthophylls are recovered.

The refined xanthophyll product resulting from the Process I method of this invention is a bright yellow, crystalline powder. It generally contains about 1600 to 2400 mg xanthophylls per pound of extracted powder. This represents a concentration factor of about 10 to 15 as compared to the original corn gluten meal. The refined xanthophylls can be used in various food stuffs, animal feeds, and pharmaceutical products or they can be, and preferably are, further purified. Conventional purification techniques can be used. Especially preferred purification techniques include adsorption chromatography and ion-exchange chromatography. Using a mixture of solvents (preferably hexane, acetone, toluene, and ethanol), the xanthophylls can be adsorbed on a silica gel and/or diatomaceous earth column. Material passing through the column can be added to recovered meal used for animal feed or can be discarded; the solvents are, however, preferably recovered and recycled. Purified xanthophylls are removed from the column using another solvent mixture (preferably hexane, acetone, and methanol). Suitable chromatographic adsorbants include silica gel, magnesium oxide, aluminumoxide, diatomaceous earth, and the like. Alternatively, the xanthophylls are absorbed on an ion exchange column using an alcohol solvent and then removed using an alcohol containing acetic acid. After removal of the solvent using conventional techniques (e.g., distillation, vacuum distillation, rotary evaporation, and the like), the yellow crystalline powder is generally expected to contain about 10,000 to 20,000 mg xanthophylls per pound of purified powder. This represents a concentration factor of about 50 to 150 as compared to the original corn gluten meal. The purified xanthophylls can be used in various foods (e.g., margarine), animal feeds (e.g., poultry feed), and pharmaceuticals as a colorant or supplement.

Figure 1:
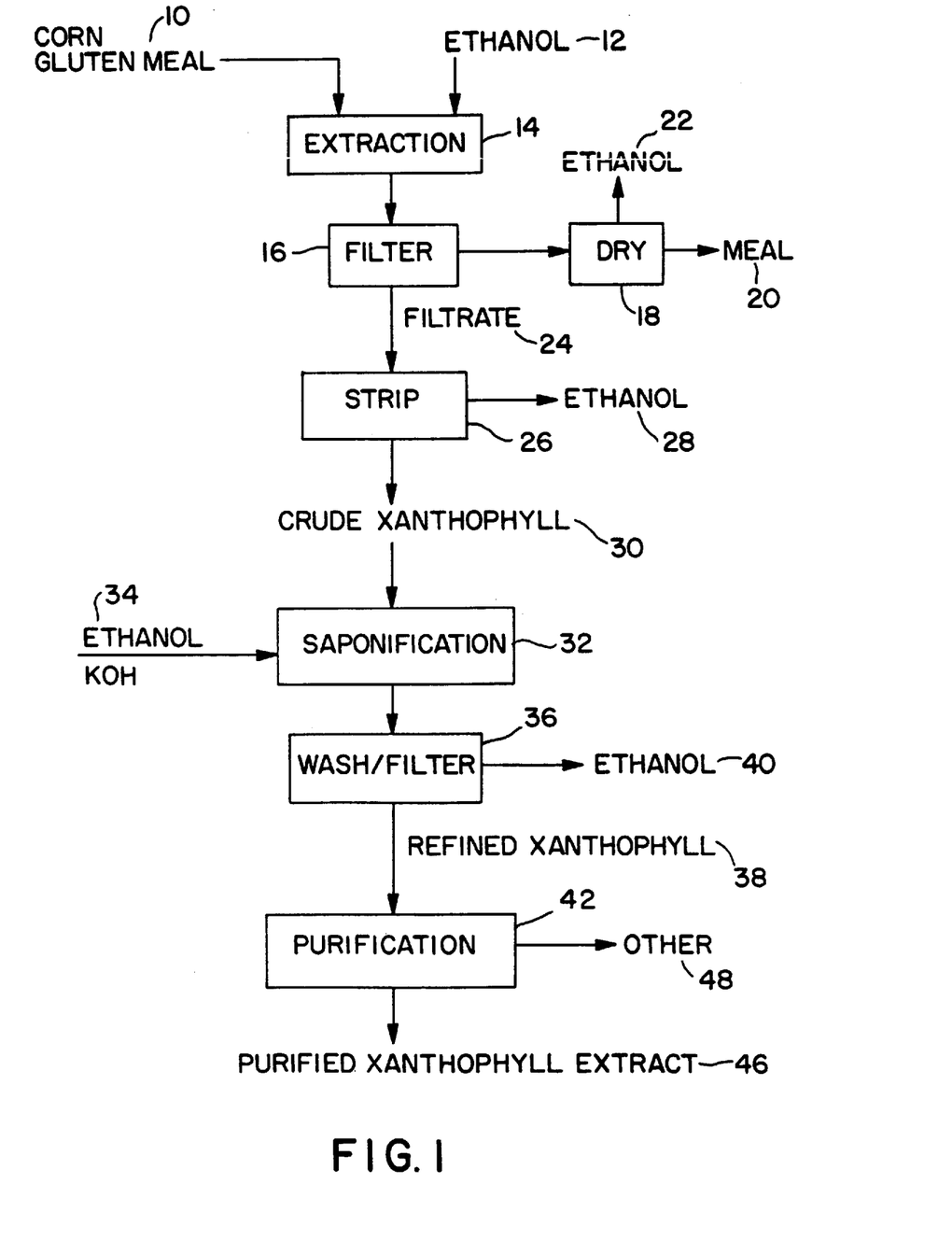
FIG. 1 is a block diagram illustrating a preferred embodiment of the Process I method of the present invention.

Referring now to FIG. 1, a preferred method of carrying out Process I of the present invention is illustrated. Corn gluten meal 10 is extracted with ethanol 12 in extraction unit 14 and then filtered in unit 16. The corn gluten meal 10 must be relatively dry (i.e., less than about 12 weight percent moisture content and preferably less than about 10 weight percent moisture content). Preferably, extraction 14 is carried out at, or close to, ambient temperatures (i.e., about 25° to 35° C.). After extraction 14 and filtration 16, the combined filtrates 24 containing xanthophylls are collected. The solids from filtration unit 16 can be collected and dried in unit 18 to generate meal 20. Meal 20 can be used in animal feeds and the like. Ethanol 22 from the drier 18 can, if desired, be recycled to extraction unit 14 or saponification unit 32.

The combined filtrates 24 are then stripped of ethanol 28 in unit 26. Stripping 26 can be accomplished by conventional means such as, for example, distillation, vacuum distillation, rotary evaporation, falling film evaporation, and the like. The stripped ethanol 28 can, if desired, be recycled to extraction unit 14 or saponification unit 32. Stripping off the ethanol results in crude xanthophylls 30. Crude xanthophylls 30 is then treated with alcoholic base 34 (preferably KOH in ethanol) in saponification unit 32. Saponification 32 converts xanthophyll esters which may be present in the crude xanthophylls 28 to free xanthophylls, thereby increasing overall yield and efficiency of xanthophyll recovery. After washing with ethanol and filtration 36, refined xanthophylls 38 are recovered. Ethanol 40 removed from the wash and filtration step 36 can, if desired, be recycled to extraction unit 14 or saponification unit 32.

Refined xanthophylls 38 can be used in this form or it can be further purified. Generally, it is preferred that the refined xanthophylls 38 are subjected to further purification. Thus, it is generally preferred that the refined xanthophylls 38 are further purified in a chromatography or cationic ion exchange column 42 using, for example, ethanol-containing solvent. The xanthophylls are absorbed on the column material and then removed using a second solvent. The removed xanthophylls are then stripped to obtain purified xanthophylls 46. Other non-absorbed materials 48 passing through the column (such as, for example, protein, starches, and fatty acids) can be added to meal 20 for use as animal feed or can be discarded. The purified xanthophyll product 46 is a bright yellow, crystalline powder which can be incorporated easily into food products, especially poultry feed products.

The following examples of the Process I method of the present invention are given to illustrate, not to limit, the Process I method of the present invention. Xanthophyll content was measured in these examples using Official Method 970.64 (Association of Official Analytical Chemists, 15th Ed., 1990).

EXAMPLE 1

This example illustrates the practice of the invention as shown in FIG. 1. Dried corn gluten meal (100 g; less than 12 weight percent water) was mixed with denatured ethanol (200 g; 0.4 weight percent water) in a flask. The solvent/meal ratio was about 2:1. The corn gluten meal contained about 160 mg xanthophylls per pound of meal. The slurried mixture was stirred vigorously to maintain a suspension for about 30 minutes at about 35° C. The mixture was then filtered and the extract collected. About 95 g of dry meal, which could be used for animal feed, was collected. After removing the ethanol from the filtrate using a rotary evaporator, 5 g of solid material was recovered as extract. This xanthophylls-containing solid material (i.e., crude xanthophylls) contained about 1150 mg xanthophylls per pound of solid. This is equivalent to about 58 mg xanthophylls per pound of meal or about 36 weight percent recovery relative to the original corn gluten meal.

The crude xanthophylls (5 g) were then refluxed with about 5 g of ethanolic KOH (about 40 g KOH in about 100 ml ethanol) for one hour. The reaction mixture was then washed with ethanol (50 ml) and filtered. The ethanol was removed from the filtrate using a rotary evaporator to yield about 4 g of solid material (i.e., refined xanthophylls) containing about 2100 mg xanthophylls per pound solid extract. This is equivalent to about 76 mg xanthophylls per pound of meal or about 47 weight percent recovery relative to the original corn gluten meal.

The refined xanthophyll product was a bright yellow crystalline powder. It could easily be incorporated into food stuffs and animal feeds.

EXAMPLE 2

Example 1 was essentially repeated except the amount of water in the ethanol used in the first extraction to produce crude xanthophylls was varied; the amount of corn gluten meal starting material was about 100 g. The following results were obtained.

| Ethanol/Water Ratio | Mass Extracted (grams) | Xanthophyll Content (mg/lb extract) |
|---|---|---|
| 100:0 | 2.9 | 1300 |
| 95:5 | 6.65 | 758 |
| 90:10 | 6.79 | 420 |
| 85:15 | 12.53 | 404 |
| 80:20 | 14.24 | 396 |
| 75:25 | 17.8 | 279 |

Figure 2:
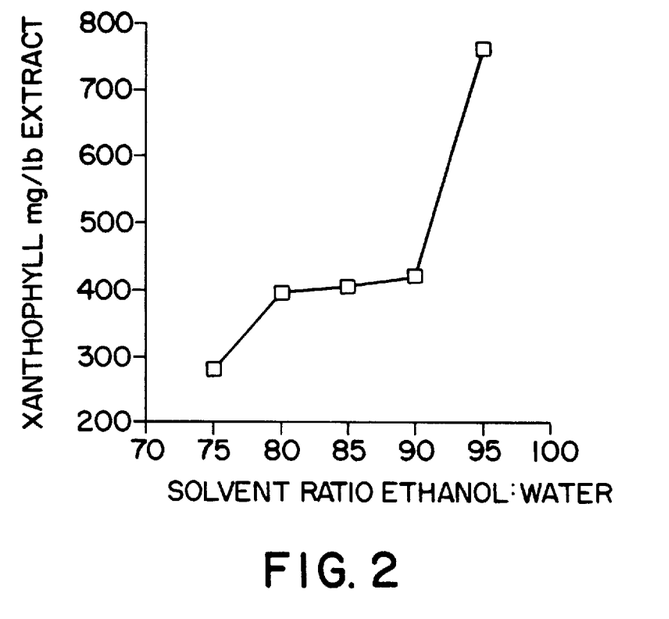
FIG. 2 is a plot of the extraction efficiency in the Process I method of the present invention of xanthophylls from corn gluten meal as a function of the water content of the ethanol used for the extraction.

This data is represented graphically in FIG. 2. As seen in FIG. 2, extraction efficiencies decrease above about 20 weight percent water. Preferably, the water content of the solvent should be kept below about 10 weight percent.

EXAMPLE 3

Figure 3:
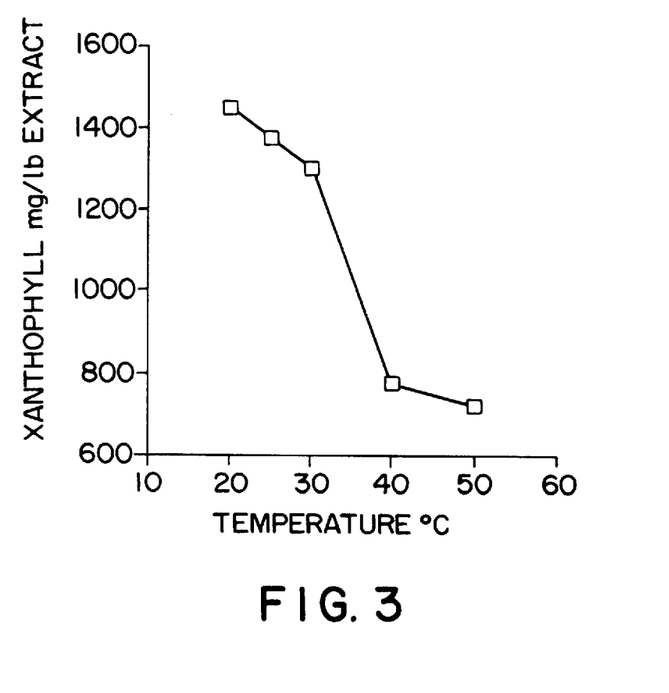
FIG. 3 is a plot of the extraction efficiency in the Process I method of the present invention of xanthophylls from corn gluten meal as a function of the temperature of the extraction.

The process of Example 1 was repeated except that the temperature of the dried corn gluten meal extraction was varied from about 200° to 50° C. The results are shown in FIG. 3. As FIG. 3 demonstrates, extraction efficiencies decrease significantly at temperatures of 40° C. and higher. Preferably, the extraction temperature should be kept between about 20° and 30° C. for maximum efficiencies.

EXAMPLE 4

Figure 4:
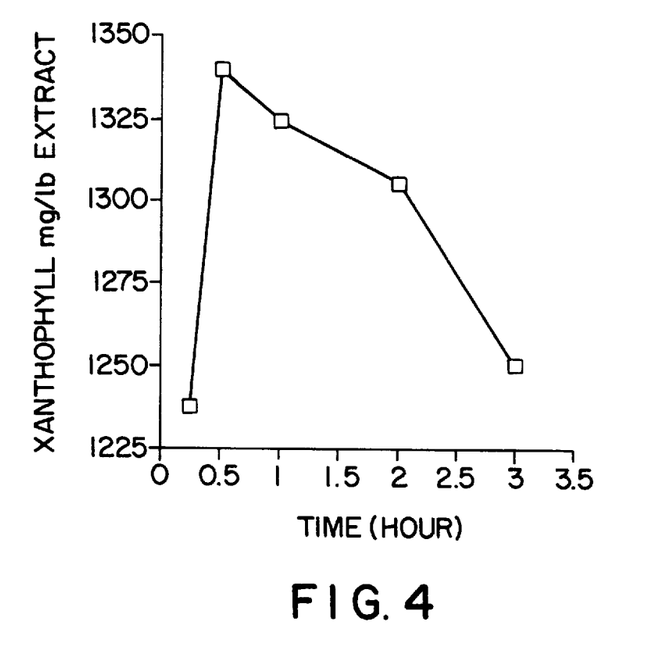
FIG. 4 is a plot of extraction efficiency in the Process I method of the present invention of xanthophylls from corn gluten meal as a function of extraction time at 25° C.

The process of Example 1 was repeated except that the length of the dried corn gluten meal extraction was varied from about 0.25 to 3 hours. The results are shown in FIG. 4. As FIG. 4 demonstrates, extraction efficiencies reach a maximum at about 30 minutes then tend to decrease with extraction times greater than about 2 hours. Thus, although longer extraction times (i.e., greater than about 2 hours) may be used, they generally do not result in significant increases in overall yields or efficiencies.

EXAMPLE 5

This example, which is included for comparative purposes only, illustrates the process described in Cook et al., U.S. Pat. No. 5,254,673, for recovery of xanthophylls from corn gluten meal. Example 1 of Cook et al. was used as a guide. A slurry was prepared with deionized water (510 ml) and corn gluten meal (120 g; the same corn gluten as used in Example 1). The slurry was heated to 80° C. and the pH was adjusted to about 6.4 using 3N NaOH. Alpha-amylase (0.5 ml) was added to the slurry with agitation. Digestion was continued for 1 hour and the slurry cooled to 50° C. The slurry was centrifuged at 1200 xg for 10 minutes and the supernate was removed. The solids were resuspended in equal parts water at 80° C. and centrifuged again at 1200 xg. The destarched solids were treated with 1M $Na_2CO_3$ and 1M $NaHCO_3$ to adjust the pH to 9 at 20° C. The resulting slurry was heated to 80° C. for 1 hour and cooled to 50° C. The slurry was centrifuged at 1200 xg for 20 minutes and the supernate was removed. The solids were resuspended in equal parts of water and neutralized with 3N HCl. The solids were centrifuged at 1200 xg for two additional times with equal parts water. The solids were then extracted with 2 volumes ethanol (4 weight percent water) for 30 minutes at room temperature and filtered. The solvent was removed by rotary evaporation. The recovered solids were a yellow paste-like or rubber-like material which contained about 141 mg xanthophylls per pound solid. Thus, the concentration of xanthophylls in the extract is essentially the same as the concentration in the original corn gluten meal (i.e., 160 mg xanthophylls per pound corn gluten meal); in other words, the Cook et al. method does not result in a concentration effect for the xanthophylls in the extract. The overall recovery of xanthophylls was about 22 percent. This example was repeated with essentially the same results. Because of the consistency and low levels of pigment in the extract, this xanthophylls-containing extract could not readily be used in food compositions, including poultry feeds.

Process II Method

The Process II method of the present invention employs the general steps of extracting corn gluten meal having a moisture content of less than about 30 weight percent (and preferably having a moisture content of less than about 20 weight percent, and more preferably having a moisture content of less than about 12 weight percent, and most preferably having a moisture content of less than about 10 weight percent) with an organic solvent (or a mixture of organic solvents) containing an antioxidant to obtain "crude xanthophylls," and then, preferably, purifying the "crude xanthophylls" to obtain purified xanthophylls.

When the "crude xanthophylls" product obtained from the extract is purified, and when the purification method employed is normal phase adsorption chromatography, which is the preferred method of purification, the additional step of removing protein from the extract containing the "crude xanthophylls" to obtain "refined xanthophylls" should be performed prior to the purification step. This protein removal step may be performed by precipitation methods, by membrane filtration or by other like methods known by those of skill in the art. The "refined xantho-phylls" may then be purified, and the purified xanthophylls product may be collected, in the same manner as is described herein for the Process II method where other purification methods are employed. This protein removal step should only be performed when the purification method employed to purify the "crude xanthophylls" contained in the extract is normal phase adsorption chromatography, and need not be performed when other purification methods are employed to purify the "crude xanthophylls" contained in the extract.

(1) Extraction

A sample of corn gluten meal is obtained and, if the corn gluten meal has a moisture content of about 30 or more weight percent, it is preferably dried to a moisture content of less than about 20 weight percent, more preferably to a moisture content of less than about 12 weight percent, and most preferably to a moisture content of less than about 10 weight percent, in the manner described hereinabove for the Process I method of the present invention.

Antioxidant is then added to an organic solvent, or to a mixture of organic solvents, in an amount of less than about 0.5 weight percent of the total xanthophylls present in the corn gluten meal being extracted, and preferably in an amount of about 0.1 weight percent. The total xanthophylls present in the corn gluten meal being extracted may be measured using the Official Method 970.64 described hereinabove, or by the modified method described hereinbelow.

The antioxidant reduces the oxidative degradation of xanthophylls, and allows the extraction to be carried out at higher temperatures, generally ranging from about 10° C. to about 80° C., and preferably ranging between about 50° and about 70° C., with about 50° C. being most preferred. Adding antioxidant, and increasing the extraction temperature, has been shown to produce xanthophyll yields in the final extract to as high as 86%.

Preferably feed grade or food grade antioxidant is used, such as ethoxyquin (6-ethoxy-1,2-dihydro-2,2,4-trimethylquinoline), propyl gallate, butylated hydroxyanisole, butylated hydroxytoluene, tertbutylhydroquinone, tocopherols, and the like.

As in the Process I method of the invention, suitable solvents include methanol, ethanol, octanol, capryl, propyl alcohols and butyl alcohols. Preferably, ethanol, or an ethanol-hexane mixture, is employed. Also as in the Process I method of the invention, the solvent (and all other reagents employed in the Process II method of the invention) preferably contains less than about 20 weight percent water and, more preferably, contains less than about 10 weight percent water, because extraction efficiencies decrease as the water content of the solvent increases above about 20 weight percent. Generally the solvent must be present in an amount sufficient to form a slurry.

The dried corn gluten meal is then extracted in the organic solvent (or mixture of organic solvents) containing the antioxidant in a ratio of at least about 2:1 solvent to corn gluten meal by weight (2:1, 3:1, 4:1, 5:1, 6:1, etc.), generally by mixing the corn gluten meal and the antioxidant-containing solvent by, for example, vigorous stirring, for a period of time ranging from about 10 minutes to about 90 minutes at a temperature ranging from 10° C. to about 80° C. Generally, the organic solvent should be present in an amount sufficient to form a slurry and, thus, the ratio of organic solvent to corn gluten meal should not be below about 2:1. The corn gluten meal may be extracted in a counter-current extraction, in a co-current extraction, by continuous extraction, by centrifugal extraction, and the like methods, which are known by those of skill in the art. The most preferred extraction technique for use in the Process II method of the invention is countercurrent extraction.

Unlike the Process I method of the invention, in which temperatures above about 40° C. should be avoided, in the extraction step of the Process II method of the invention, it is preferable to use temperatures above about 49° C.

The xanthophyll extract at this stage of the process (without purification) generally contains from about 500 to about 2,000 mg xanthophylls per pound of dried extract. This represents a concentration factor of about 5 to 20 as compared to the original corn gluten meal.

As is shown in Example 1 presented hereinbelow, extractions carried out at 50° C. with a 3:1 solvent to corn gluten meal ratio, using technical grade ethanol, have yielded dried extracts containing 799 mg of xanthophylls per pound of dried extract (without being purified).

As is shown in Example 2 presented hereinbelow, using a solvent which is a mixture of 20:80 hexane:ethanol has yielded dried extracts with xanthophyll concentrations of 1140 mg of xanthophylls per pound of dried extract (without being purified).

As is shown in Example 4 presented hereinbelow, a solvent which is a mixture of 40:60 hexane:ethanol has produced purified dried extracts containing 1410 mg of xanthophylls per pound of dried extract (without being purified).

The extraction may be performed in one step, or the extraction may be performed in a series of separate extractions in which the antioxidant-containing organic solvent (or mixture of organic solvents) is divided into two, three, four or more lots, as has been done in Example 5 described hereinbelow In the latter case, the corn gluten meal may be separately extracted with each of the lots of solvent in the same manner as if only one such extraction were occurring. After each of the separate extractions is separately performed, the xanthophyll-containing extracts are combined. It is preferable to perform the extraction in a series of separate extractions because this procedure simulates a countercurrent extraction, and results in higher yields of crude xanthophylls.

After the mixing has been completed, the xanthophylls-containing extract (or a combination of extracts resulting from a series of separate extractions carried out with divided amounts of the antioxidantcontaining solvent or mixture of solvents) is collected by, for example, filtering it to remove insoluble materials from the extract, and to obtain "crude xanthophylls." Alternatively, it may be collected by centrifugation, hydroclone or by other like methods known by those of skill in the art. The resulting extract contains "crude xanthophylls" which can be used in this form in various foodstuffs, animal feeds and pharmaceutical products, or they can be, and preferably are, purified.

As is described in Example 6, the extract may be dried, for example, by rotary evaporation, and then the dried extract may be extracted one or more additional times in the same or different organic solvent (or mixture of organic solvents) prior to purification.

(2) Purification
   (a) Protein Removal
   The removal of protein from the extract containing "crude xanthophylls" should only be performed when normal phase adsorption chromatography is used as the method for purifying the "crude xanthophylls" product resulting from the extraction. This is the preferred method for purifying the xanthophylls product resulting from the extraction. Other methods of purification, such as partition (reverse phase) adsorption chromatography, ion exchange chromatography, size exclusion chromatography and countercurrent chromatography, which may alternatively be employed, do not require this step.

Protein makes up the major portion of the corn gluten meal extract containing the "crude xanthophylls." Prior to purification by normal phase adsorption chromatography, the organic solvent is removed by conventional techniques known by those of skill in the art, such as by distillation, vacuum distillation, sparging, rotary evaporation and the like, and the extract is dissolved in a non-polar solvent, such as hexane. Because the protein is not soluble in hexane, it can clog the chromatography column and, thereby, interfere with xanthophyll purification.

Several methods of protein removal may be employed, including precipitation and membrane filtration.

Protein precipitation can be achieved by adding a reagent, such as ammonium sulphate, to the extract that forces the protein out of solution. For instance, adding a solvent that the protein is not soluble in, such as acetone, ethyl acetate and the like, can force the protein to precipitate. Concentrating the extract (i.e. stripping off part of the organic solvent prior to precipitating the protein) is not necessary, but may be done. The precipitate formed, which will consist mainly of protein, is then removed, for example, by filtration, or by other methods known by those of skill in the art, such as centrifugation or hydroclone. The resulting soluble portion of the extract contains "refined xanthophylls." Conventional techniques known by those of skill in the art, such as by distillation, vacuum distillation, sparging, rotary evaporation, and the like, may be employed to dry the filtrate. However, it is not necessary to dry the filtrate prior to the purification procedure.

A membrane can also be used to separate the protein from the other components in the extract. The protein has been found by gel electrophoresis to have a molecular weight range of between 20,000 and 25,000 daltons. Membranes are available that can separate the lower molecular weight components, such as xanthophylls (molecular weight of 568.85), from the higher molecular weight components, such as proteins. Companies such as Millipore Corporation and PCI Membrane Systems produce membranes that have molecular weight cutoffs of 20,000 or lower. In such a system, the organic solvent extract is pumped through a membrane system, and the protein will remain in the concentrate while the xanthophylls, as well as the triglycerides and fatty acids, will go into the permeate. The organic solvent is then stripped off of the permeate by convention stripping methods, and the permeate is fractionated by normal phase adsorption chromatography.

(b) Purification
   The "crude xanthophylls" product contained in the extract described hereinabove (when a purification method other than normal phase adsorption chromatography is employed to purify the "crude xanthophylls" product), or the "refined xanthophylls" product obtained after the protein removal procedures described hereinabove (when normal phase adsorption chromatography is employed to purify the "crude xanthophylls" product contained in the extract) may then be purified.

The "refined xanthophylls" may be purified by normal phase adsorption chromatography, and the "crude xanthophylls" may be purified by partition (reverse phase) adsorption chromatography, ion exchange chromatography, size exclusion chromatography, countercurrent chromatography and like methods, which are known by those of skill in the art.

Normal phase adsorption chromatography is described in the following references: K. Robards, et al., *Principles and*

*Practice of Modern Chromatographic Methods*, Academic Press (1995); Scott, R. P. W., *Liquid Chromatography Column Theory*, John Wiley and Sons, Inc., New York (1992); Scott, R. P. W., *Techniques and Practices of Chromatography*, Marcel Dekker, Inc., New York (1995); L. R. Snyder, et al., *Introduction to Modern Liquid Chromatography* (2nd Edition), John Wiley and Sons, Inc., New York (1979); and Unger, K. K., *Packing and Stationary Phases in Chromatographic Techniques*, Marcel Dekker, Inc., New York (1990).

Partition (reverse phase) chromatography is described in the following references: El Rassi, et al., "Reversed Phase and Hydrophobic Interaction Chromatography of Peptides and Proteins," in: *Separation Processes in Biotechnology*, Marcel Dekker, Inc., New York (1990); and Unger, K. K., *Packaging and Stationary Phases in Chromatographic Techniques*, Marcel Dekker, Inc., New York (1990).

Ion exchange chromatography is described in the following references: Shuey, Charles D., "Ion Exchange Processes", in: *Separation Processes in Biotechnology*, Marcel Dekker, Inc., New York (1990); Small, H., *Ion Chromatography*, Plenum Press (1989); Unger, K. K., *Packaging and Stationary Phases in Chromatographic Techniques*, Marcel Dekker, Inc., New York (1990); and Wankat, Phillip C., "Large Scale Chromatography", in: *Handbook of Separation Process Technology*, John Wiley and Sons, Inc., New York (1987).

Size exclusion chromatography is described in Unger, K. K., *Packaging and Stationary Phases in Chromatographic Techniques*, Marcel Dekker, Inc., New York (1990).

Countercurrent chromatography is described by Walter D. Conway, et al., *Modern Countercurrent Chromatography*, American Chemical Society, Washington, D.C. (1995).

Each of the references concerning chromatography which is described hereinabove is incorporated in its entirety herein by reference.

For normal phase adsorption chromatography, which is the preferred method of purification, suitable adsorbents (stationary phases) which may be employed include silica gel, magnesium oxide, aluminum oxide, cellulose, sucrose, starch, calcium oxide, calcium phosphate, calcium carbonate, potassium carbonate, sodium carbonate and the like. Mixtures of these adsorbents, such as a mixture of silica gel and magnesium oxide, a preferred absorbent, may also be used.

Adsorbent to "refined xanthophylls" dry weight ratios as low as 2:1 and as high as 100:1 have been used successfully to purify the "refined xanthophylls." Thus, such a dry weight ratio of adsorbent to "refined xanthophylls" may be from about 2:1 to about 100:1 of adsorbent to "refined xanthophylls." Preferably, a dry weight ratio of 2:1 adsorbent to "refined xanthophylls" is used.

The "refined xanthophylls" are adsorbed onto the stationary phase. If necessary or desired, they can be is solubilized in a small amount of the eluting solvent (mobile phase) prior to adsorption onto the column bed. The chromatography column is then eluted with an organic solvent or an organic solvent mixture of two or more solvents in order to remove the purified xanthophylls product from the column.

The column may be eluted with an isocratic solvent (i.e., the same solvent or solvent mixture is used throughout the elution process), or a gradient or stepwise gradient elution may be used (i.e., the solvent or solvent mixture composition is changed over the course of the elution).

In the case of an isocratic solvent system, the chromatography column is eluted with an organic solvent or an organic solvent mixture. Depending on the solvents being used, a non-polar solvent or solvent mixture such as hexane, cyclohexane, heptane, petroleum ether and the like would make up 100 to 50% of the solvent or solvent mixture. This may be modified with 0 to 50% of a more polar solvent or solvent mixture, such as ethyl acetate, acetone, isopropyl alcohol, ethanol, methanol, butanol, and the like. Anywhere from 5 to 200 column volumes of mobile phase may be required to elute the column, and the appropriate amount may be determined by a person of skill in the art.

Fractions are collected off of the column. Fractions containing triglycerides and fatty acids may be added back to the extracted corn gluten meal. The xanthophyll esters fraction may be combined with the free xanthophylls fraction, or saponified, and then combined with the free xanthophylls fraction. The free xanthophylls fraction may be used as a poultry feed supplement, or may be purified further. If a protein fraction is collected, it can also be added back to the extracted corn gluten meal.

Alternatively, the column may be eluted with a gradient or stepwise gradient solvent system. After the "refined xanthophylls" are adsorbed onto the stationary phase, the column is eluted with an organic solvent or an organic solvent mixture. Over time, the composition of the mobile phase will change in a continuous or a stepwise fashion, such that the polarity of the mobile phase is increased. For instance, the initial mobile phase would be 100 to 50% non-polar solvent or solvent mixture, including solvents such as hexane, cyclohexane, heptane, petroleum ether, and the like. This may be modified with 0 to 50% of a more polar solvent or solvent mixture including solvents such as ethyl acetate, acetone, isopropyl alcohol, ethanol, methanol, butanol, and the like. The percentage of the more polar solvent or solvent mixture is then increased at a given rate, or in a stepwise fashion, in a manner known by those of skill in the art. The percentage of one or more of the more polar solvents or solvent mixture may be increased to make up 0 or 100% of the mobile phase, or any value in between. From 5 to 200 column volumes of mobile phase may be required to elute the column, and the appropriate amount may be determined by a person of skill in the art.

For example, the "refined xanthophylls" mixture may be adsorbed onto a silica gel column using a volume to volume ratio of 97 to 3 hexane to acetone. Triglycerides, carotenes and xanthophyll esters are eluted off of the chromatography column with this solvent mixture, but the free "refined xanthophylls" remain adsorbed to the column. A more polar solvent mixture, such as a solvent mixture having a volume to volume ratio of hexane:acetone anywhere from 94:6 to 0:100 may be used to elute the purified xanthophylls from the chromatography column.

The purified free xanthophylls fraction may then be dried by any of the methods described hereinabove, and/or known by those of skill in the art, and the concentration of the purified xanthophylls in the dried fraction may then be calculated by the Official Method 970.64 described hereinabove, or by the modified version of this method described hereinbelow.

Regardless of the purification method employed, additional purification by chromatography may be performed to increase the purity of the final purified xanthophylls product. This additional chromatography may use chromatography columns which include normal phase adsorbents, as described hereinabove, or reverse phase adsorbents, such as the bonded phase adsorbents octadecylsilane(C18), octylsilane(C8), butylsilane (C4), cyanopropylsilane (CN), aminopropylsilane (NH2), and the like. Solvents which may be employed with reverse phase adsorbents include water, methanol, acetonitrile, acetone, ethanol, isopropanol, ethyl acetate, hexane, and the like. Other chromatography methods, such as ion exchange chromatography, size exclusion chromatography, partition chromatography and countercurrent chromatography, may also be employed to increase the purity of the xanthophylls product.

The purified xanthophylls product resulting from the Process II method of this invention is in the form of an orange or red paste. It is generally expected to contain from about 5,000 to about 60,000 mg xanthophylls per pound of purified product. This represents a concentration factor as high as about 600 as compared to the concentration of xanthophylls present in the original corn gluten meal (from about 100 to 200 mg xanthophylls per pound of meal). This purified xanthophylls product may be used in the manner described hereinabove with respect to the Process I method of the invention.

Figure 5:
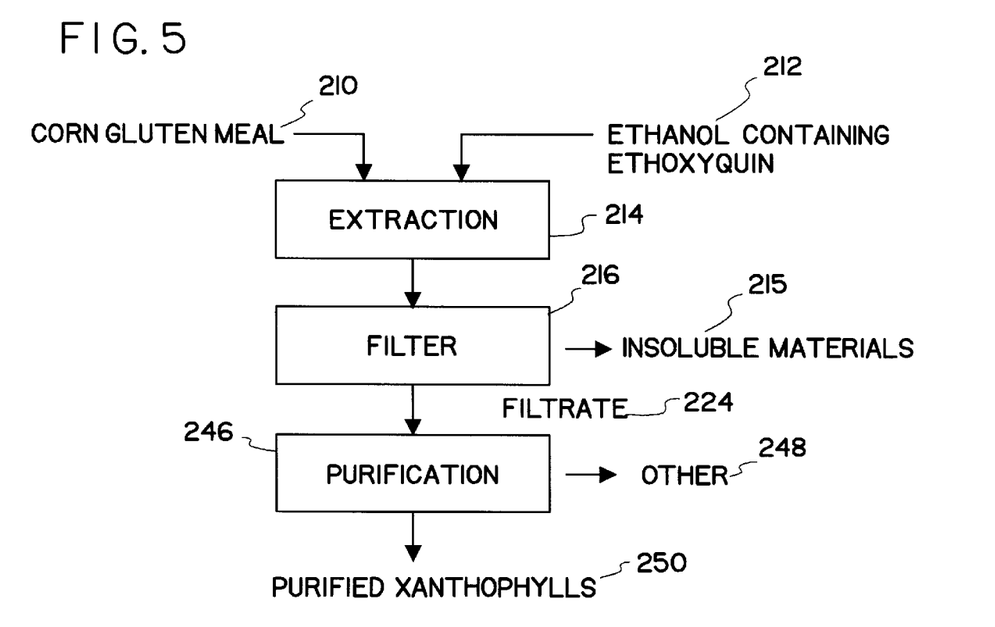
FIGS. 5 and 5A are block diagrams illustrating two preferred embodiments of the Process II method of the present invention.

Referring now to FIG. 5, a preferred method of carrying out the Process II method of the present invention is illustrated.

Corn gluten meal 210 is extracted with ethanol containing ethoxyquin 212 antioxidant in an amount of about 0.1 weight percent of the total xanthophylls present in the corn gluten meal 210 in extraction unit 214. The resulting extract is then collected as a filtrate 224 by filtering the insoluble materials 215 from this extract in filter unit 216. The corn gluten meal 210 should be relatively dry (i.e., less than about 30 weight percent moisture content and, preferably, less than about 20 weight percent moisture content and, more preferably, less than about 12 weight percent moisture content and, most preferably, less than about 10 weight percent moisture content). Preferably, extraction 214 is carried out at about 50° C.

The crude xanthophylls which are present in the filtrate 224 can be used in this form, or can be further purified. Generally, it is preferred that the crude xanthophylls are subjected to further purification 246. It is generally preferred that the crude xanthophylls are further purified in a chromatography column using, for example, ethanol-containing solvent, in order to produce purified xanthophylls 250. The xanthophylls may be adsorbed on the column material and then removed using a second solvent to obtain purified xanthophylls 250. Other non-adsorbed materials passing through the column 248 (such as, for example, protein, starches, and fatty acids) can be added to corn gluten meal for use as animal feed or can be discarded. The purified xanthophylls product 250 is in the form of an orange or red paste which can easily be incorporated into food products, especially poultry feed products. For example, it can be dissolved in a solid or liquid carrier, such as water, spray dried into a product and mixed therewith by methods known by those of skill in the art.

Figure 5A:
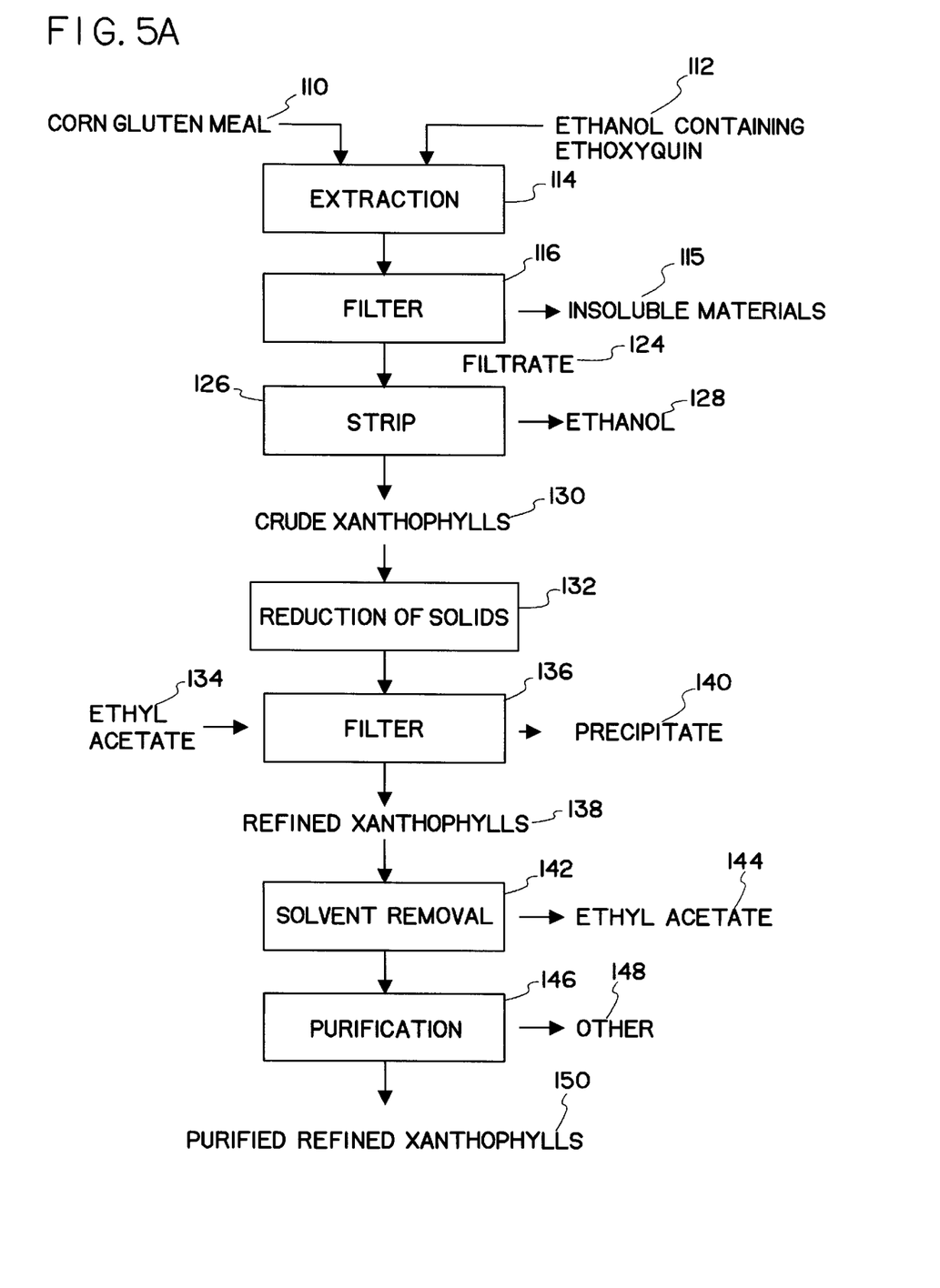

Referring now to FIG. 5A, another preferred method of carrying out the Process II method of the present invention is illustrated.

Corn gluten meal 110 is extracted with ethanol containing ethoxyquin 112 antioxidant in an amount of about 0.1 weight percent of the total xanthophylls present in the corn gluten meal 110 in extraction unit 114. The resulting extract is then collected by filtering the insoluble materials 115 from this extract in filter unit 116. The corn gluten meal 110 should be relatively dry, as is described with respect to FIG. 5 hereinabove. Preferably, extraction 114 is carried out at about 50° C.

After the above extraction and filtration, the filtrate 124 is then preferably stripped of ethanol 128 in unit 126. Stripping may be accomplished in the manner described hereinabove for the Process I method of the present invention. Stripping off the ethanol 128 results in an extract containing "crude xanthophylls" 130.

Crude xanthophylls 130 can be used in this form or can be further purified. Generally, it is preferred that the crude xanthophylls 130 are subjected to further purification. Thus, it is generally preferred that the crude xanthophylls 130 are further purified in a chromatography column using, for example, ethanol-containing solvent. The xanthophylls are adsorbed on the column material and then removed using a second solvent. The removed xanthophylls are then stripped to obtain purified xanthophylls. Other non-adsorbed materials passing through the column (such as, for example, protein, starches, and fatty acids) can be added to corn gluten meal for use as animal feed or can be discarded.

The extract containing "crude xanthophylls" 130 is then preferably reduced with reduction unit 132 to a total solids concentration ranging from about 10 to about 40 weight percent with a rotary evaporator or other like equipment.

A second organic solvent, which is preferably ethyl acetate 134, is then preferably added to the extract containing the "crude xanthophylls" in a 1:1 solvent: extract ratio by weight. The extract is preferably mixed with the solvent at a temperature of 25° C. for a period of 30 seconds with vigorous stirring.

The precipitate 140 which is formed in the above step, which consists mainly of protein, is then removed with filter unit 136. The remaining soluble portion of the extract contains "refined xanthophylls" 138.

The ethyl acetate solvent 144 is then preferably removed from the soluble portion of the extract containing refined xanthophylls 138 in, preferably, rotary evaporation unit 142.

The refined xanthophylls 138 are further purified by normal phase adsorption chromatography 146 using 1:1 silica gel:magnesium oxide as adsorbent, hexane as an organic solvent to adsorb the refined xanthophylls on the chromatography column material, and ethanol as a second solvent to remove the purified refined xanthophylls 150 from the chromatography column. Other adsorbed materials 148 passing through the column, such as protein, starches, fatty acids and triglycerides, can be added to animal feed, or can be discarded. The purified refined xanthophylls product 150 is in the form of an orange or red paste which can easily be incorporated into food products, especially poultry feed products, as is described hereinabove with respect to FIG. 5.

The following examples are given to illustrate, and not to limit, the Process II method of the present invention. As in the examples presented hereinabove for the Process I method of the present invention, xanthophylls content throughout the different steps described in the examples illustrating the Process II method of the present invention was measured using Official Method 970.64 described hereinabove. However, in the example illustrating the Process II method of the present invention, a VWR Denatured Alcohol (Fisher Scientific catalog number VW0475-3) has been employed in place of the Absolute ethanol in the extractant. This formulation, which is described below, has been determined by comparative study to provide equivalent results.

| Formulation | |
|---|---|
| SD I Alcohol | 100 volumes |
| Methyl Isobutyl Ketone | 1 volume |
| Ethyl Acetate | 1 volume |
| Hydrocarbon Solvent | 1 volume |

Additionally, a 97:3 hexane:acetone carotene eluent has been employed in place of the 96:4 hexane:acetone carotene eluent because the 97:3 hexane:acetone was found to permit a better separation of the first xanthophylls band (monohydroxy pigments). Finally, prior to reading the absorbance of an aliquot of the xanthophyll solution produced, the aliquot has been centrifuged. This has been found to improve the precision of analysis, possibly by clarifying the solution.

EXAMPLE 1

Corn gluten meal (100 g) containing less than 12 weight percent moisture, and containing 170 mg of xanthophylls, was extracted at 50° C. for 30 minutes, with stirring, in 300 g of ethanol containing the antioxidant ethoxyquin. The corn gluten meal was recovered by vacuum filtration and extracted two more times in the same manner. The total amount of ethoxyquin used was equivalent to 0.1% of the amount of xanthophyll present in the corn gluten meal as determined by the Official Method 970.64 described hereinabove. The three extracts were combined and dried by rotary evaporation. The xanthophyll concentration in the dried extract was determined by the Official Method 970.64 described hereinabove to be 799 mg/lb (without being purified), which was about a 5-fold increase from the amount of xanthophylls present in the original (starting) corn gluten meal.

EXAMPLE 2

Corn gluten meal (100 g) containing less than 12 weight percent moisture, and containing 170 mg of xanthophylls, was extracted at 60° C. for 30 minutes, with stirring, in 200 g of 20:80 hexane:ethanol (w/w) containing the antioxidant ethoxyquin. The corn gluten meal was recovered by vacuum filtration and extracted two more times in the same manner. The total amount of ethoxyquin used was equivalent to 0.1% of the amount of xanthophyll present in the corn gluten meal as determined by the Official Method 970.64 described hereinabove. The three extracts were combined and dried by rotary evaporation. The xanthophyll concentration in the dried extract was determined by the Official Method 970.64 described hereinabove to be 1140 mg/lb (without being purified), which was about a 7-fold increase from the amount of xanthophylls present in the original (starting) corn gluten meal

EXAMPLE 3

Corn gluten meal (100 g) containing 20 weight percent moisture, and containing 170 mg of xanthophylls, was extracted at 60° C. for 30 minutes, with stirring, in 300 g of ethanol containing the antioxidant ethoxyquin. The corn gluten meal was recovered by vacuum filtration and extracted two more time in the same manner. The total amount of ethoxyquin used was equivalent to 0.1% of the amount of xanthophyll present in the corn gluten meal as determined by the Official Method 970.64 described hereinabove. The three extracts were combined and dried by rotary evaporation. The xanthophyll concentration in the dried extract was determined by the Official Method 970.64 described hereinabove to be 549 mg/lb (without being purified), which was about a 3-fold increase from the amount of xanthophylls present in the original (starting) corn gluten meal.

EXAMPLE 4

Corn gluten meal (100 g) containing less than 12 weight percent moisture, and containing 170 mg of xanthophylls, was extracted at 60° C. for 30 minutes, with stirring in 200 g of 40:60 hexane:ethanol containing the antioxidant ethoxyquin. The corn gluten meal was recovered by vacuum filtration and extracted two more times in the same manner. The total amount of ethoxyquin used was equivalent to 0.1% of the amount of xanthophyll present in the corn gluten meal as determined by the Official Method 970.64 described hereinabove. The three extracts were combined and dried by rotary evaporation. The xanthophyll concentration in the dried extract was determined by the Official Method 970.64 described hereinabove to be 1410 mg/lb (without being purified), which was about an 8-fold increase from the amount of xanthophylls present in the original (starting) corn gluten meal.

EXAMPLE 5

Extraction 100 g of dried corn gluten meal (corn gluten meal having less than 12 weight percent water) were weighed into an extraction vessel.

The total amount of xanthophyll present in the dried corn gluten meal (in grams) was then calculated using the Official Method 970.64 described hereinabove. Because the corn gluten meal had an xanthophyll concentration of 170 mg xanthophylls per pound of corn gluten meal, 100 g of corn gluten meal contained 37.4 mg of xanthophyll. The amount of ethoxyquin antioxidant added to the ethanol solvent employed was 0.1% of 37.4 mg, which is equivalent to 37.4 $\mu$g.

In a 3:1 solvent to corn gluten meal batch extraction, the antioxidant was divided between three, 300 g, portions of 96% ethanol (0.4% weight percent water).

The first 300 g portion of ethanol was poured into the extraction vessel with the dried corn gluten meal, and the extraction was carried out with vigorous stirring at 50° C. for 30 minutes. The extract was recovered by vacuum filtration.

The corn gluten meal was returned to the extraction vessel. The second portion of ethanol was poured over the corn gluten meal, and a second similar extraction was performed with mixing at 50° C. for 30 minutes. The extract was once again recovered by vacuum filtration.

The corn gluten meal was returned to the extraction vessel and extracted in a similar manner with the third and final portion of ethanol. The extraction was performed with mixing at 50° C. for 30 minutes. The final extract was recovered by vacuum filtration.

The three extracts described above were combined. The combined extracts weighed 713.74 g, and contained 16.81 g total solids (2.36 weight percent solids). (A 10.0 g sample of the combined extracts was dried by rotary evaporation and determined to weigh 0.236 g. Based upon this value, the amount of total solids in the combined extract was determined.) The resulting dry weight "crude xanthophyll" concentration was determined by the Official Method 970.64 described hereinabove, and was determined to be 799 mg per pound of extract (prior to purification).

Protein Removal

Part of the ethanol was removed by rotary evaporation, such that the weight of the extract was reduced from 713.74 g to 156.23 g. The concentrate then contained 10.8 weight percent solids.

Ethyl acetate containing 0.004 percent water was added to the concentrate at a 2 to 1 weight percent solvent to concentrate ratio, such that 312.5 g of ethyl acetate was added to the concentrate. A yellow-white precipitate, consisting mainly of protein, then formed. The precipitate was then removed by vacuum filtration.

The solvent was removed from the filtrate by rotary evaporation. The dried filtrate, which contained "refined xanthophylls," was determined to have an xanthophylls concentration of 2150 mg of xanthophylls per pound of dried filtrate by the Official Method 970.64 described hereinabove.

Normal Phase Adsorption Chromatography

A small glass chromatography column, 30 mm ID×60 mm, was packed with 12 g of 1:1 silica gel (Devisil grade 633 type 60A) 60:magnesium oxide (Fisher Scientific hyflo super cel).

The refined xanthophylls (i.e. the dried filtrate) was dissolved in 175 g of hexane (containing no water) and adsorbed onto the chromatography column.

The column was eluted with 79 g of hexane:acetone (containing 0.02% weight percent water), 97:3 (v:v), followed by 100 g of acetone (containing 0.5 weight percent water).

Three fractions were collected from the column: (1) a hexane fraction; (2) a 97:3 hexane:acetone fraction; and (3) an acetone fraction.

Each of the fractions was dried by rotary evaporation. The hexane fraction dry weight was determined to be 3.53 g, with an xanthophylls concentration of 205 mg per pound of solid fraction, as determined using the Official Method 970.64 described hereinabove. The 97:3 hexane:acetone fraction dry weight was determined to be 0.85 g, with an xanthophyll concentration of 820 mg per pound of solid fraction, as determined using the Official Method 970.64 described hereinabove. These two fractions contained mostly oil, fatty acids, carotein and xanthophylls esters, and could be added back to recovered meal used for animal feed, or could be discarded. The last fraction, which was the acetone fraction, had a dry weight of 1.32 g, with a purified xanthophylls concentration of 7430 mg per pound of solid fraction, as determined using the Official Method 970.64 described hereinabove and was in the form of an orange/red paste.

Thus, after the process described above was completed, the xanthophylls concentration present in the corn gluten meal had increased from 170 mg of xanthophylls per pound of the original corn gluten meal to 7430 mg of xanthophylls per pound of dried purified extract, which was about a 44-fold increase.

EXAMPLE 6

Corn gluten meal (300 g) containing less than 12 weight percent moisture, and containing 170 mg of xanthophylls, was extracted at 60° C. for 30 minutes, with stirring, in 900 g of ethanol containing the antioxidant ethoxyquin. The corn gluten meal was recovered by vacuum filtration and extracted three more times in the same manner. The total amount of ethoxyquin used was equivalent to 0.3% of the amount of xanthophyll present in the corn gluten meal as determined by the Official Method 970.64 described hereinabove. The three extracts were combined and dried by rotary evaporation. The xanthophyll concentration in the dried extract was determined by the Official Method 970.64 described hereinabove to be 596 mg/lb (prior to purification).

A portion of the dried extract, 55.7 g, was dissolved in 100 ml of ethanol. Hexane (500 ml) and acetone (100 ml) were added to the extract and the solution was partitioned, in a 1 L separatory funnel, with 300 ml of aqueous 10% sodium sulfate solution. The hexane layer was removed and the aqueous layer was extracted two more times with 500 ml of hexane. The three hexane phases were combined and dried by rotary evaporation. The xanthophyll concentration was determined by the Official Method 970.64 described hereinabove to be 1716 mg/lb.

A chromatography column, 1" ID×25", was packed with 78 g of 1:1 silica gel:magnesium oxide (Devisil grade 633 type 60A silica gel and Fisher Scientific hyflo super cel magnesium oxide). The feed, weighing 7.33 g dry weight with an xanthophyll concentration of to 1716 mg/lb, consisted of the combined hexane phase from above. The feed was dissolved in 246 g of hexane and adsorbed onto the column. The column was then eluted with hexane (69 g), followed by 97:3 hexane:acetone (515 g), 70:15:15 hexane:acetone:methanol (384 g), and methanol (212 g). The xanthophyll fraction weighed 0.2 g dry weight and had an xanthophyll concentration of 30,760 mg/lb, as determined by the Official Method 970.64 described hereinabove, which was about a 180-fold increase from the amount of xanthophylls present in the original (starting) corn gluten meal.

EXAMPLE 7

Corn gluten meal (100 g) containing 15% weight percent moistures and containing 170 mg of xanthophylls, was extracted at 60° C. for 30 minutes, with stirring, in 300 g of ethanol containing the antioxidant ethoxyquin. The corn gluten meal was recovered by vacuum filtration and extracted two more times in the same manner. The total amount of ethoxyquin used was equivalent to 0.1% of the amount of xanthophyll present in the corn gluten meal as determined by the Official Method 970.64 described hereinabove. The three extracts were combined and samples from the extract were removed and dried by rotary evaporation. The xanthophyll concentration in the dried extract was determined by the Official Method 970.64 described hereinabove to be 600 mg/lb (prior to purification).

The combined extract was stripped by rotary evaporation, to a concentration of 41% total solids (as determined by drying a 10.0 ml sample). Ethyl acetate (132 g) was added to the extract and the mixture was stirred with a spatula for one or two minutes. The mixture was vacuum filtered to remove the precipitate. The filtrate was dried by rotary evaporation and determined, by the Official Method 970.64 described hereinabove, to have an xanthophyll concentration of 1835 mg/lb.

A chromatography column, 32 mm ID×30 mm, was packed with 9.4 g of 1:1 silica gel:magnesium oxide (Devisil grade 633 type 60A silica gel and Fisher Scientific hyflo super cel magnesium oxide). The feed, weighing 4.7 g dry weight with an xanthophyll concentration of 1835 mg/lb, consisted of the ethyl acetate soluble portion of the corn gluten meal ethanol extract from above. The feed was dissolved in 5 g of 97:3 hexane:ethyl acetate and adsorbed onto the column. The column was then eluted with hexane (40 g), followed by ethyl acetate (55 g). The xanthophyll fraction weighed 0.9 g dry weight and had an xanthophyll concentration of 8,320 mg/lb, as determined by the Official Method 970.64 described hereinabove, which was about a 49-fold increase from the amount of xanthophylls present in the original (starting) corn gluten meal.

EXAMPLE 8

Corn gluten meal (300 g) containing less than 12 weight percent moisture, and containing 170 mg of xanthophylls, was extracted at 60° C. for 30 minutes, with stirring, in 900 g of ethanol containing the antioxidant ethoxyquin. The corn gluten meal was recovered by vacuum filtration and extracted two more times in the same manner. The total amount of ethoxyquin used was equivalent to 0.1% of the amount of xanthophyll present in the corn gluten meal as determined by the Official Method 970.64 described hereinabove. The three extracts were combined and samples from the extract were removed and dried by rotary evaporation. The xanthophyll concentration in the dried extract was determined by the Official Method 970.64 described hereinabove to be 470 mg/lb (prior to purification).

The combined extract was stripped by rotary evaporation to a concentration of 54% weight percent (as determined by drying a 10.0 ml sample). Ethyl acetate (400 g) was added to the extract (100 g) and the mixture was stirred with a spatula for 15 minutes. The mixture was vacuum filtered to remove the precipitate. The filtrate was dried by rotary evaporation and determined by the Official Method 970.64 described hereinabove to have an xanthophyll concentration of 1518 mg/lb.

A chromatography column, 30 mm ID×60 mm, was packed with 16.5 g of 1:1 silica gel:magnesium oxide (Devisil grade 633 type 60A silica gel and Fisher Scientific hyflo super cel magnesium oxide). A portion of the dried filtrate weighing 8.35 g dry weight was dissolved in 70 g of hexane and adsorbed onto the column. The column was then eluted with hexane (90 g), followed by 97:3 hexane:ethyl acetate (98 g), ethyl acetate (142 g), and ethanol (118 g). The xanthophyll fraction weighed 2.32 g dry weight and had an xanthophyll concentration of 5150 mg/lb, as determined by using the Official Method 970.64 described hereinabove.

A chromatography column, 1" ID×26", was packed with 80.0 g of 1:1 silica gel:magnesium oxide (Devisil grade 633 type 60A silica gel and Fisher Scientific hyflo super cel magnesium oxide). The feed consisted of a portion of the xanthophyll fraction from the previous column weighing 1.57 g dry weight with an xanthophyll concentration of 5,150 mg/lb, as determined by the Official Method 970.64 described hereinabove. The feed was dissolved in 15 g of 96:4 hexane:isopropyl alcohol and adsorbed onto the column. The column was then eluted with 96:4 hexane:isopropyl alcohol (518 g), followed by 90:10 hexane:isopropyl alcohol (197 g), and isopropyl alcohol (174 g). The xanthophyll fraction weighed 0.35 g dry weight and had an xanthophyll concentration of 9,307 mg/lb, as determined by the Official Method 970.64 described hereinabove, which was about a 55-fold increase from the amount of xanthophylls present in the original (starting) corn gluten meal.

While the present invention has been described herein with some specificity, and with reference to certain preferred embodiments thereof, those of ordinary skill in the art will recognize numerous variations, modifications, and substitutions of that which has been described which can be made, and which are within the scope and spirit of the invention. It is intended therefore that all of these modifications and variations be within the scope of the present invention as described and claimed herein, and that the invention be limited only by the scope of the claims which follow, and that such claims be interpreted as broadly as is reasonable.

That which is claimed is:

1. A method for recovering xanthophylls from corn gluten meal comprising:
    (a) extracting corn gluten meal containing less than about 30 weight percent moisture with an organic solvent, or an organic solvent mixture, containing an amount of antioxidant which is less than about 0.5 weight percent of the total amount of xanthophylls present in the corn gluten meal in a ratio of at least about 2:1 of organic solvent, or organic solvent mixture, to corn gluten meal; and
    (b) collecting the resulting extract to obtain said xanthophylls.

2. The method of claim 1 wherein said corn gluten meal contains less than about 20 weight percent moisture and is mixed with said organic solvent, or organic solvent mixture, for a period of time ranging from about 10 minutes to about 90 minutes at a temperature ranging from about 10° C. to about 80° C.

3. The method of claim 2 wherein said corn gluten meal contains less than about 12 weight percent moisture.

4. The method of claim 3 wherein said organic solvent contains less than about 20 weight percent water.

5. The method of claim 4 wherein said organic solvent is methanol, ethanol, octanol, capryl, propyl alcohol, butyl alcohol or an ethanol-hexane mixture.

6. The method of claim 5 wherein said antioxidant is ethoxyquin, propyl gallate, butylated hydroxyanisole, butylated hydroxytoluene, tertbutylhydroquinone or a tocopherol.

7. The method of claim 6 wherein said organic solvent is ethanol or an ethanol-hexane mixture.

8. The method of claim 7 wherein said ethanol or ethanol-hexane mixture contains less than about 10 weight percent water, and contains an amount of said antioxidant which is about 0.3 weight percent or less of the total amount of xanthophylls present in said corn gluten meal.

9. The method of claim 8 wherein said antioxidant is ethoxyquin.

10. The method of claim 9 wherein said corn gluten meal is mixed with said ethanol or ethanol-hexane mixture at a temperature ranging from about 50° C. to about 70° C.

11. The method of claim 4 wherein said extraction is performed in a series of two or more separate extractions or in a countercurrent extraction.

12. The method of claim 6 wherein said extraction is performed in a series of two or more separate extractions or in a countercurrent extraction.

13. A method for recovering xanthophylls from corn gluten meal comprising:
    (a) extracting corn gluten meal containing less than about 30 weight percent moisture with an organic solvent, or an organic solvent mixture, containing an amount of antioxidant which is less than about 0.5 weight percent of the total amount of xanthophylls present in the corn gluten meal in a ratio of at least about 2:1 of organic solvent, or organic solvent mixture, to corn gluten meal;
    (b) collecting the resulting extract to obtain crude xanthophylls;
    (c) purifying the crude xanthophylls; and
    (d) collecting the purified xanthophylls.

14. The method of claim 13 wherein said corn gluten meal contains less than about 20 weight percent moisture and is mixed with said organic solvent, or organic solvent mixture, for a period of time ranging from about 10 minutes to about 90 minutes at a temperature ranging from about 10° C. to about 80° C.

15. The method of claim 14 wherein said corn gluten meal contains less than about 12 weight percent moisture.

16. The method of claim 15 wherein said organic solvent contains less than about 20 weight percent water.

17. The method of claim 16 wherein protein is removed from said extract containing crude xanthophylls to obtain refined xanthophylls, and said refined xanthophylls are purified by normal phase adsorption chromatography.

18. The method of claim 17 wherein said protein is removed by precipitation or membrane filtration, the adsorbent employed in said chromatography is a mixture of silica gel and magnesium oxide, hexane, hexane:isopropyl alcohol or isopropyl alcohol is employed in said chromatography to adsorb said refined xanthophylls on said adsorbent, and ethanol, methanol, hexane, hexane:acetone, acetone, hexane:acetone:methanol, hexane:ethyl acetate, ethyl acetate or hexane:isopropyl alcohol is employed in said chromatography to remove the purified xanthophylls from the chromatography column.

19. The method of claim 16 wherein said crude xanthophylls are purified by partition (reverse phase) adsorption chromatography, ion exchange chromatography, size exclusion chromatography or countercurrent chromatography.

20. The method of claim 17 wherein said organic solvent is methanol, ethanol, octanol, capryl, propyl alcohol, butyl alcohol or an ethanol-hexane mixture and said antioxidant is ethoxyquin, propyl gallate, butylated hydroxyanisole, butylated hydroxytoluene, tertbutylhydroquinone or a tocopherol.

21. The method of claim 19 wherein said organic solvent is methanol, ethanol, octanol, capryl, propyl alcohol, butyl alcohol or an ethanol-hexane mixture and said antioxidant is ethoxyquin, propyl gallate, butylated hydroxyanisole, butylated hydroxytoluene, tertbutylhydroquinone or a tocopherol.

22. The method of claim 20 wherein said organic solvent is ethanol or an ethanol-hexane mixture which contains less than about 10 weight percent water, and contains an amount of ethoxyquin which is about 0.3 or less weight percent of the total amount of xanthophylls present in said corn gluten meal.

23. The method of claim 21 wherein said organic solvent is ethanol or an ethanol-hexane mixture which contains less than about 10 weight percent water, and contains an amount of ethoxyquin which is about 0.3 or less weight percent of the total amount of xanthophylls present in said corn gluten meal.

24. The method of claim 22 wherein said corn gluten meal is mixed with said ethanol or ethanol-hexane mixture at a temperature ranging from about 50° C. to about 70° C.

25. The method of claim 23 wherein said corn gluten meal is mixed with said ethanol or ethanol-hexane mixture at a temperature ranging from about 50° C. to about 70° C.

26. The method of claim 24 wherein said extraction is performed in a series of two or more separate extractions or in a countercurrent extraction.

27. The method of claim 25 wherein said extraction is performed in a series of two or more separate extractions or in a countercurrent extraction.

28. The method of claim 26 wherein said corn gluten meal is mixed with said ethanol or ethanol-hexane mixture at a temperature of about 50° C., said protein is removed by precipitation or membrane filtration, the adsorbent employed in said chromatography is a mixture of silica gel and magnesium oxide, hexane, hexane:isopropyl alcohol or isopropyl alcohol is employed in said chromatography to adsorb said refined xanthophylls on said adsorbent, and ethanol, methanol, hexane, hexane:acetone, acetone, hexane:acetone:methanol, hexane:ethyl acetate, ethyl acetate or hexane:isopropyl alcohol is employed in said chromatography to remove the purified xanthophylls from the chromatography column.

29. The method of claim 27 wherein said corn gluten meal is mixed with said ethanol or ethanol-hexane mixture at a temperature of about 50° C.

30. The method of claim 28 wherein hexane is employed to adsorb said refined xanthophylls on said adsorbent and ethanol is employed to remove the purified xanthophylls from said chromatography column.

31. A method for recovering xanthophylls from corn gluten meal comprising:
 (a) drying a sample of corn gluten meal to a moisture content of less than about 30 weight percent;
 (b) adding an amount of antioxidant to an organic solvent, or to an organic solvent mixture, which is less than about 0.5 weight percent of the total amount of xanthophylls present in the sample of corn gluten meal;
 (c) extracting the sample of corn gluten meal with the organic solvent, or organic solvent mixture, by mixing a ratio of organic solvent, or organic solvent mixture, to corn gluten meal of at least about 2:1 for a period of time ranging from about 10 minutes to about 90 minutes at a temperature ranging from about 10° C. to about 80° C.;
 (d) collecting the resulting extract to obtain crude xanthophylls;
 (e) purifying the crude xanthophylls; and
 (f) collecting the purified xanthophylls.

\* \* \* \* \*